United States Patent
Kapelushnik et al.

(10) Patent No.: US 9,719,937 B2
(45) Date of Patent: Aug. 1, 2017

(54) DIAGNOSIS OF CANCER

(75) Inventors: Joseph Kapelushnik, Neve Ilan (IL); Shaul Mordechai, Omer (IL); Ilana Nathan, Omer (IL); Udi Zelig, D.N. Negev (IL); Rami Zigdon, Ra'anana (IL)

(73) Assignee: TODOS MEDICAL LTD., Airport (IL)

( * ) Notice: Subject to any disclaimer, the term of this patent is extended or adjusted under 35 U.S.C. 154(b) by 0 days.

(21) Appl. No.: 14/116,506

(22) PCT Filed: May 10, 2012

(86) PCT No.: PCT/IL2012/000187
§ 371 (c)(1),
(2), (4) Date: Feb. 4, 2014

(87) PCT Pub. No.: WO2012/153326
PCT Pub. Date: Nov. 15, 2012

(65) Prior Publication Data
US 2014/0166884 A1    Jun. 19, 2014

Related U.S. Application Data

(60) Provisional application No. 61/484,753, filed on May 11, 2011.

(51) Int. Cl.
*G01N 21/84*    (2006.01)
*A61B 5/00*    (2006.01)
(Continued)

(52) U.S. Cl.
CPC .......... *G01N 21/84* (2013.01); *A61B 5/0075* (2013.01); *G01N 21/35* (2013.01); *G01J 3/42* (2013.01); *G01N 2021/3595* (2013.01)

(58) Field of Classification Search
CPC .... G01N 21/84; G01N 21/3595; G01N 33/48; G01N 21/35; G01N 2021/3595; G01J 3/42; A61B 5/0075
(Continued)

(56) References Cited

U.S. PATENT DOCUMENTS 4,832,483 A    5/1989  Verma
4,912,050 A *  3/1990  Fossel .................. G01R 33/465
                                                  324/300

(Continued)

FOREIGN PATENT DOCUMENTS

WO    2009/074988    6/2009
WO    2011/121588    10/2011
(Continued)

OTHER PUBLICATIONS

U.S. Appl. No. 61/350,073, filed Jun. 1, 2010.
(Continued)

*Primary Examiner* — David Porta
*Assistant Examiner* — Blake Riddick
(74) *Attorney, Agent, or Firm* — Sughrue Mion, PLLC

(57) ABSTRACT

A method is provided including obtaining an infrared (IR) spectrum of a blood plasma sample by analyzing the blood plasma sample by infrared spectroscopy, and based on the infrared spectrum, generating an output indicative of the presence of a solid tumor or a pre-malignant condition. Other applications are also described.

15 Claims, 4 Drawing Sheets

(51) Int. Cl.
*G01N 21/35* (2014.01)
*G01J 3/42* (2006.01)
*G01N 21/03* (2006.01)

(58) Field of Classification Search
USPC .................. 250/339.08, 339.02, 339.07
See application file for complete search history.

(56) References Cited

U.S. PATENT DOCUMENTS

| | | | |
|---|---|---|---|
| 5,197,470 A | | 3/1993 | Helfer et al. |
| 5,261,410 A | * | 11/1993 | Alfano et al. ............... 600/475 |
| 5,697,373 A | | 12/1997 | Richards-Kortum et al. |
| 5,733,739 A | | 3/1998 | Zakim et al. |
| 5,734,587 A | * | 3/1998 | Backhaus ............ B01L 3/5085 382/133 |
| 5,945,675 A | * | 8/1999 | Malins ..................... G01J 3/45 250/339.08 |
| 6,251,616 B1 | | 6/2001 | Barbera-Guillem |
| 6,274,871 B1 | | 8/2001 | Dukor et al. |
| 6,642,012 B1 | | 11/2003 | Ashdown |
| 6,841,388 B2 | * | 1/2005 | Dukor et al. .................. 436/64 |
| 7,524,681 B2 | | 4/2009 | Wolf et al. |
| 7,611,839 B2 | | 11/2009 | Twine |
| 8,173,433 B2 | | 5/2012 | Folkman et al. |
| 2001/0000150 A1 | * | 4/2001 | Malins ..................... C12Q 1/68 435/6.14 |
| 2002/0027649 A1 | | 3/2002 | Chudner |
| 2004/0073011 A1 | | 4/2004 | Hagay et al. |
| 2004/0110221 A1 | | 6/2004 | Twine et al. |
| 2004/0186383 A1 | | 9/2004 | Rava et al. |
| 2005/0017179 A1 | | 1/2005 | Mordechai et al. |
| 2006/0194211 A1 | | 8/2006 | Burczynski |
| 2007/0003921 A1 | * | 1/2007 | Andrus ............................ 435/4 |
| 2007/0282190 A1 | | 12/2007 | Dekel et al. |
| 2009/0004682 A1 | * | 1/2009 | Kitamura et al. .............. 435/14 |
| 2009/0175819 A1 | * | 7/2009 | Priest et al. ................. 424/85.2 |
| 2010/0021039 A1 | | 1/2010 | Ortyn et al. |
| 2010/0185064 A1 | * | 7/2010 | Bandic ................. A61B 5/0059 600/306 |
| 2010/0210023 A1 | * | 8/2010 | Wong et al. .................... 436/90 |
| 2010/0273191 A1 | * | 10/2010 | Arber ............... G01N 33/57407 435/7.23 |
| 2011/0028808 A1 | * | 2/2011 | Kuratsune ............ A61B 5/0059 600/322 |
| 2011/0182881 A1 | * | 7/2011 | Chin et al. ................. 424/130.1 |
| 2013/0137134 A1 | | 5/2013 | Mordechai |
| 2013/0143258 A1 | | 6/2013 | Kapelushnik et al. |
| 2014/0087397 A1 | * | 3/2014 | Romick-Rosendale ....... G01N 33/57484 435/7.92 |

FOREIGN PATENT DOCUMENTS

| | | |
|---|---|---|
| WO | 2011/151825 | 12/2011 |
| WO | 2012/153326 | 11/2012 |

OTHER PUBLICATIONS

An International Search Report and a Written Opinion both dated Nov. 29, 2011, which issued during the prosecution of Applicant's PCT/IL2011/000426.
An International Preliminary Report on Patentability dated Dec. 4, 2012, which issued during the prosecution of Applicant's PCT/IL2011/000426.
An International Search Report and a Written Opinion both dated Aug. 3, 2011, which issued during the prosecution of Applicant's PCT/IL2011/000282.
An International Search Report and a Written Opinion both dated Aug. 31, 2012, which issued during the prosecution of Applicant's PCT/IL2012/000187.
An International Preliminary Report on Patentability dated Nov. 12, 2013, which issued during the prosecution of Applicant's PCT/IL2012/000187.
Agatha G., et al., Fatty acid composition of lymphocyte membrane phospholipids in children with acute leukemia. Cancer Lett. Nov. 28, 2001;173(2):139-44.
Arakawa H., et al., Silver (I) complexes with DNA and RNA studied by Fourier transform infrared spectroscopy and capillary electrophoresis. Biophys J. Sep. 2001;81(3):1580-7.
Argov S., et al., Diagnostic potential of Fourier-transform infrared microspectroscopy and advanced computational methods in colon cancer patients. J Biomed Opt. Apr. 2002;7(2):248-54.
Argov S, Sahu RK, Bernshtain E, Salman A, Shohat G, Zelig U, Mordechai S. Inflammatory bowel diseases as an intermediate stage between normal and cancer: a FTIR-microspectroscopy approach.
Backhaus J., et al., Diagnosis of breast cancer with infrared spectroscopy from serum sample. Vibrational Spectroscopy 52(2010) 173-177.
Beyer M., and Schulze J. L., Regulatory T cells in cancer. Blood. Aug. 1, 2006;108(3):804-11.
Bogomolny E., et al., Early spectral changes of cellular malignant transformation using Fourier transformation infrared microspectroscopy. 2007. J Biomed Opt.12:024003.
Boydston-White ST., et al., 1999, Infrared spectroscopy of human tissue V infrared spectroscopic studies of myeloid leukemia (ML-1) cells at different phases of cell cycle. Biospectroscopy 5:219-227.
Coates RJ, et al., Diagnostic markers for ovarian cancer screening: not ready for routine clinical use. Clin Cancer Res. Nov. 15, 2008;14(22):7575-6.
Curie TJ., et al., Specific recruitment of regulatory T cells in ovarian carcinoma fosters immune privilege and predicts reduced survival. Nat Med. Sep. 2004;10(9):942-9.
Diem M., et al., A decade of Vibrational micro-spectroscopy of human cells and tissue (1994-2004). Analyst 129,88-885 (2004).
Duffy MJ. Role of tumor markers in patients with solid cancers: A critical review. Eur J Intern Med. May 2007;18(3):175-184.
Fabian H., et al., Diagnosing benign and malignant lesions in breast tissue sections by using IR-microspectroscopy. Biochim Biophys Acta. Jul. 2006;1758(7):874-82.
Gazi E., et al., Biomolecular profiling of metastatic prostate cancer cells in bone marrow tissue using FTIR microspectroscopy: a pilot study. Anal Bioanal Chem. Mar. 2007;387(5):1621-31.
Gottfried EL., Lipids of human leukocytes: relation to celltype. J Lipid Res. Jul. 1967;8(4):321-7.
Graser A., et al., Comparison of CT colonography, colonoscopy, sigmoidoscopy and faecal occult blood tests for the detection of advanced adenoma in an average risk population. Gut. Feb. 2009;58(2):241-8.
Handy B. The Clinical Utility of Tumor Markers. LabMedicine. Feb. 2009; 40, 99-103.
Hammody Z., et al., Distinction of malignant melanoma and epidermis using IR micro-spectroscopy and statistical methods. Analyst. Mar. 2008;133(3):372-8.
Hildebrand J., et al., Neutral glycolipids in leukemic and nonleukemic leukocytes. J Lipid Res. May 1971;12(3):361-6.
Inbar M., et al., Cholesterol as a bioregulator in the development and inhibition of leukemia. Proc Natl Acad Sci USA. Oct. 1974;71(10):4229-31.
Inbar M., et al., Fluidity difference of membrane lipids in human normal and leukemic lymphocytes as controlled by serum components. Cancer Res. Sep. 1977;37(9):3037-41.
Kanika Singh., et al., Spectroscopic techniques as a diagnostic tool for early detection of osteoporosis. Journal of Mechanical Science and Technology vol. 24, No. 8, 1661-1668.
Khanmohammadi M., et al., Diagnosis of basal cell carcinoma by infrared spectroscopy of whole blood samples applying soft independent modeling class analogy. J Cancer Res Clin Oncol. Dec. 2007;133(12):1001-10. Epub Aug. 2, 2007.
Kiviniemi MT., et al., Decision making about cancer screening: an assessment of the state of the science and a suggested research agenda from the ASPO Behavioral Oncology and Cancer Communication Special Interest Group. Cancer Epidemiol Biomarkers Prev. Nov. 2009;18(11):3133-7.

(56) References Cited

OTHER PUBLICATIONS

Krafft C., et al., Identification of primary tumors of brain metastases by SIMCA classification of IR spectroscopic images. Biochim Biophys Acta. Jul. 2006;1758(7):883-91.

Kriat M., et al., Analysis of plasma lipids by NMR spectroscopy: application to modifications induced by malignant tumors. J Lipid Res. Jun. 1993;34(6):1009-19.

Leong PP., et al., Phenotyping of lymphocytes expressing regulatory and effector markers in infiltrating ductal carcinoma of the breast. Immunol Lett. Feb. 15, 2006;102(2):229-36.

Liu Kz., et al., Bimolecular characterization of leucocytes by infrared spectroscopy. Br J Haematol. Mar. 2007;136 (5):713-22.

Liu Z., et al., Tumor regulatory T cells potently abrogate antitumor immunity. J Immunol. May 15, 2009;182(10):6160-7.

Liyanage UK., et al., Prevalence of regulatory T cells is increased in peripheral blood and tumor microenvironment of patients with pancreas or breast adenocarcinoma. J Immunol. Sep. 1, 2002;169(5):2756-61.

Lyman DJ., et al., Fourier transform infrared attenuated total reflection analysis of human hair: comparison of hair from breast cancer patients with hair from healthy subjects. Appl Spectrosc. Jan. 2005;59(1):26-32.

Mitchell PS., et al., Circulating microRNAs as stable blood-based markers for cancer detection. PNAS Jul. 29, 2008 vol. 105 No. 30 10513-10518.

Cazzaniga G, Biondi A. Molecular monitoring of childhood acute lymphoblastic leukemia using antigen receptor gene rearrangements and quantitative polymerase chain reaction technology. Haematologica. Mar. 2005;90(3):382-90.

Mordechai S., et al., Possible common biomarkers from FTIR microspectroscopy of cervical cancer and melanoma. J Microsc. Jul. 2004;215(Pt 1):86-91.

Naumann D. FT-infrared and FT-Raman spectroscopy in bio-medical research, Appl. Spectrosc. Rev. 36, 239-298 (2001).

Pavlou MP, Diamandis EP. The cancer cell secretome: a good source for discovering biomarkers? J Proteomics. Sep. 10, 2010;73(10):1896-906.

Petibois C., et al., Plasma protein contents determined by Fourier-transform infrared spectrometry. Clin Chem. Apr. 2001;47(4):730-8.

Petibois C., et al., Analytical performances of FT-IR spectrometry and imaging for concentration measurements within biological fluids, cells, and tissues. Analyst. May 2006;131(5):640-7.

Campana D. Molecular determinants of treatment response in acute lymphoblastic leukemia. Hematology Am Soc Hematol Educ Program. 2008:366-73.

Petter CH., et al., Development and application of Fourier-transform infrared chemical imaging of tumour in human tissue. Curr Med Chem. 2009;16(3):318-26.

Ransohoff DF. Rules of evidence for cancer molecular-marker discovery and validation. Nat Rev Cancer. Apr. 2004;4(4):309-14.

Sahu RK., et al., Detection of abnormal proliferation in histologically 'normal' colonic biopsies using FTIR-microspectroscopy. Scand J Gastroenterol. Jun. 2004;39(6):557-66.

Sahu RK., et al., Can Fourier transform infrared spectroscopy at higher wavenumbers (mid IR) shed light on biomarkers for carcinogenesis in tissues? J Biomed Opt. Sep.-Oct. 2005;10(5):054017.

Sahu RK., et al., Continuous monitoring of WBC (biochemistry) in an adult leukemia patient using advanced FTIR-spectroscopy. Leuk Res. Jun. 2006;30(6):687-93.

Sasada T., et al., CD4+CD25+ regulatory T cells in patients with gastrointestinal malignancies: possible involvement of regulatory T cells in disease progression. Cancer. Sep. 1, 2003;98(5):1089-99.

Saslow D., et al., American Cancer Society Breast Cancer Advisory Group. American Cancer Society guidelines for breast screening with MRI as an adjunct to mammography. CA Cancer J Clin. Mar.-Apr. 2007;57(2):75-89. Erratum in: CA Cancer J Clin. May-Jun. 2007;57(3):185.

Shaw RA., et al., Multianalyte serum analysis using mid-infrared spectroscopy. Ann Clin Biochem. Sep. 1998;35 ( Pt 5):624-32.

Shimokawara I., et al., Identification of lymphocyte subpopulations in human breast cancer tissue and its significance: an immunoperoxidase study with anti-human T- and B-cell sera. Cancer. Apr. 1, 1982;49(7):1456-64.

Smith RA., et al., Cancer screening in the United States, 2010: a review of current American Cancer Society guidelines and issues in cancer screening. CA Cancer J Clin. Mar.-Apr. 2010;60(2):99-119.

Spiegel, R J., et al., 1982. Plasma lipids alterations in leukemia and lymphoma. Am. J. Med. 72: 775-781.

Tokuno K., et al., Increased prevalence of regulatory T-cells in the peripheral blood of patients with gastrointestinal cancer. Anticancer Res. May 2009;29(5):1527-32.

Toyran N., et al., Selenium alters the lipid content and protein profile of rat heart: an FTIR microspectroscopy study. Arch. Biochem.Biophys. 2007 458:184-193.

Whitehead RH., et al., T and B lymphocytes in breast cancer stage relationship and abrogation of T-lymphocyte depression by enzyme treatment in vitro. Lancet. Feb. 14, 1976;1(7955):330-3.

Whitford P., et al., Flow cytometric analysis of tumour infiltrating lymphocytes in breast cancer. Br J Cancer. Dec. 1990;62(6):971-5.

Wieczorek G., et al., Quantitative DNA methylation analysis of FOXP3 as a new method for counting regulatory T cells in peripheral blood and solid tissue. Cancer Res. Jan. 15, 2009;69(2):599-608.

Wolf AM., et al., Increase of regulatory T cells in the peripheral blood of cancer patients. Clin Cancer Res. Feb. 2003;9(2):606-12.

Zelig U., et al., Diagnosis of cell death by means of infrared spectroscopy. Biophys J Oct. 7, 2009;79:2107-14.

Zhang SL, et al., Vibrational Spectra and Experimental Assignments of Thymine and Nine of its Isotopomers J. Phys. Chem. A. 102 (1998), p. 461.

An Office Action dated Aug. 19 ,2013, which issued during the prosecution of U.S. Appl. No. 13/638,367.

Ramesh et al. Novel Methodology for the Follow-Up of Acute Lymphoblastic Leukemia Using FTIR Microspectroscopy; Journal of Biochemical and Biophysical Methods, vol. 51 (2002) pp. 251-261.

Mohlenhoff et al. Mie-Type Scattering and Non-Beer-Lambert absorption behavior of human cells in infrared microspectroscopy.

Bogomolny et al. "Monitoring of viral cancer progression using FTIR microscopy: A comparative study of intact cells and tissues."

Visintin, Irene, et al.: "Diagnostic Markers for Early Detection of Ovarian Cancer", Clin Cancer Res 2008; 14:1065-1072, DOE10. 1158/1078-0432.CCR-07-1569, Published online Feb. 7, 2008.

Hengartner, M. O. The biochemistry of apoptosis. Nature. 2000, 407: 770-776.

Andrus PG. Cancer monitoring by FTIR spectroscopy. Technol Cancer Res Treat. Apr. 2006;5(2):157-67.

Lavie Y, et al., Changes in membrane microdomains and caveolae constituents in multidrug-resistant cancer cells. Lipids. 1999;34 Suppl:S57-63.

Vrooman LM, Silverman LB. Childhood acute lymphoblastic leukemia: update on prognostic factors. Curr Opin Pediatr. Feb. 2009;21(1):1-8.

Krishna CM., et al., Combined Fourier transform infrared and Raman spectroscopic approach for identification of multidrug resistance phenotype in cancer cell lines. Biopolymers. Aug. 5, 2006;82(5):462-70.

Basso G, et al., Risk of relapse of childhood acute lymphoblastic leukemia is predicted by flow cytometric measurement of residual disease on day 15 bone marrow. J Clin Oncol. Nov. 1, 2009;27(31):5168-74.

Pui CH, Evans WE. Treatment of acute lymphoblastic leukemia. N Engl J Med 2006; 354: 166-78.

Tucci F, Aricò M. Treatment of pediatric acute lymphoblastic leukemia. Haematologica. Aug. 2008;93(8):1124-8.

Castillo L. A Randomized Trial of the I-BFM-SG for the Management of Childhood non-B Acute Lymphoblastic Leukemia. All IC-BFM 2002.

U.S. Appl. No. 61/318,395, filed Mar. 29, 2010.

(56) References Cited

OTHER PUBLICATIONS

Smith M, et al., Uniform approach to risk classification and treatment assignment for children with acutelymphoblastic leukemia. J Clin Oncol. Jan. 1996;14(1):18-24. PubMed PMID: 8558195.
Mehrotra et al., Analysis of ovarian tumor pathology by Fourier Transform Infrared Spectroscopy, Journal of Ovarian Research, 2010, vol. 3, No. 27, p. 1-6.
Devi et al., FTIR Spectroscopic Analysis of Normal and Cancerous Human Breast Tissues between 450 Cm-1 and 1100 Cm-1 using Trend Analysis, International Journal of ChemTech Research, Sep. 2010, vol. 2, No. 3, pp. 1426 to 1433.
Schultz et al., Study of Chronic Lymphocytic Leukemia Cells by FT-IR Spectroscopy and Cluster Analysis, Pergamon, Leukemia Research, 1996, vol. 20, No. 8, pp. 649 to 655.
Big Medicine Encyclopedia. Ed. Petrovskiy, vol. 12, 1980, 13 pages total.
An English translation of RU 2 352 256.
An English translation of a communication, issued by the Russian Patent Office in corresponding Russian Application No. 2012157998.
International Search Report with Written Opinion dated Apr. 23, 2014, issued by the International Searching Authority in corresponding International Application No. PCT/IL13/050945.
European Search Report dated Oct. 10, 2014, which issued during the prosecution of Applicant's European App No. 12782256.7.
Khanmohammadi et al., Chemometrics assisted investigation of variations in infrared spectra of blood samples obtained from women with breast cancer: a new approach for cancer diagnosis, Eur J Cancer Care, 2010, vol. 19, pp. 352 to 359.
Krishna et al, Characterisation of uterine sarcoma cell lines exhibiting MDR phenotype by vibrational spectroscopy, Biochimica et Biophysica Acta (BBA), Elsevier, 2005, General Subjects vol. 1726, Issue 2, pp. 160 to 167.
Khanmohammadi et al., Cancer Diagnosis by Discrimination between Normal and Malignant Human Blood Samples Using Attenuated Total Reflectance-Fourier Transform Infrared Spectroscopy, Informa Healthcare, Cancer Investigation, 2007, vol. 25, pp. 397 to 404.
Bosschaart et al., "A literature review and novel theoretical approach on the optical properties of whole blood", Lasers Med Sci, 2014, vol. 29, pp. 453-479.
Meinke et al., "Optical propertied of platelets and blood plasma and their influence on the optical behavior of whole blood in the visible to near infrared wavelength range", J Biomed Opt, Jan.-Feb. 2007, vol. 12, No. 1, pp. 014024 (Abstract).
An Office Action dated Jun. 8, 2015, which issued during the prosecution of U.S. Appl. No. 14/116,506.
Wood et al. Fourier Transform Infrared Spectroscopy As a Method for Monitoring the Molecular Dynamics of Lymphocyte Activation; Applied Spectroscopy, vol. 54, No. 3 (2000) pp. 353-359.
Applicant response dated Jan. 20, 2015, to Office Action issued on Sep. 18, 2014, which issued during the prosecution of U.S. Appl. No. 13/701,262.
Interview Summary Report dated Jan. 26, 2015, which issued during the prosecution of U.S. Appl. No. 13/701,262.
Interview Summary Report dated Jan. 22, 2014, which issued during the prosecution of U.S. Appl. No. 13/701,262.
Interview Summary Report dated Sep. 4, 2015, which issued during the prosecution of U.S. Appl. No. 13/701,262.
Applicant response dated Sep. 8, 2015, to Office Action issued on Mar. 6, 2015, which issued during the prosecution of U.S. Appl. No. 13/701,262.
An Office Action dated Mar. 6, 2015, which issued during the prosecution of U.S. Appl. No. 13/701,262.
An Office Action dated Nov. 2, 2015, which issued during the prosecution of U.S. Appl. No. 13/701,262.
An Office Action dated Oct. 16, 2013, which issued during the prosecution of U.S. Appl. No. 13/701,262.
An Office Action dated Sep. 18, 2014, which issued during the prosecution of U.S. Appl. No. 13/701,262.
An Office Action dated Feb. 24, 2014, which issued during the prosecution of U.S. Appl. No. 13/701,262.
U.S. Appl. No. 61/484,753, filed May 11, 2011.
Applicant response dated Aug. 25, 2014, to Office Action issued on Feb. 24, 2014, which issued during the prosecution of U.S. Appl. No. 13/701,262.
Applicant response dated Jan. 16, 2014, to Office Action issued on Oct. 16, 2013, which issued during the prosecution of U.S. Appl. No. 13/701,262.
An Office Action in U.S. Appl. No. 13/701,262 dated May 12, 2016.
Applicant's response dated Nov. 14, 2016 to the Office Action issued on May 12, 2016 in U.S. Appl. No. 13/701,262.
A Supplemental Notice of Allowability issued in U.S. Appl. No. 13/701,262 on Feb. 8, 2017.
Bitar, Renata Andrade et al.: "Biochemical analysis of human breat tissues using FT-Raman spectroscopy," Laboratory of Biomedical Vibrational Spectroscopy, 2006.
Gao, Tiyu et al.: "Human breast carcionmal tissues display distinctive FTIR spectra: Implication for the histological characterization of carcinomas," Department of Chemistry, Peking University, Beijing 100871, China, Feb. 17, 1999.
An Office Action in U.S. Appl. No. 14/894,128 dated Nov. 17, 2016.
An Extended European Search Report issued in EP 13885931.9 dated Jan. 26, 2017.

\* cited by examiner

DIAGNOSIS OF CANCER

CROSS-REFERENCES TO RELATED APPLICATIONS

The present application is a U.S. national phase of PCT Application no. PCT/IL2012/000187 to Kapelushnik et al., filed May 10, 2012, which published as WO 2012/153326 to Kapelushnik et al., and which claims the priority of U.S. Provisional Patent Application 61/484,753 to Kapelushnik et al., entitled, "Diagnosis of cancer," filed May 11, 2011, which is incorporated herein by reference.

FIELD OF EMBODIMENTS OF THE INVENTION

Embodiments of the present invention relate generally to diagnosis and monitoring of a disease, and particularly to methods for diagnosis and monitoring of a malignant disease.

BACKGROUND

Analysis of certain markers (e.g., certain proteins, peptides, RNA molecules) in a patient's circulation may be useful in detection and/or monitoring of cancer. For example, studies have shown that analysis of a patient's blood plasma for certain oncofetal antigens, enzymes and/or miRNA molecules may assist in diagnosis and prognosis of certain types of cancer.

Fourier Transform Infrared (FTIR) spectroscopy is typically used to identify biochemical compounds and examine the biochemical composition of a biological sample. Typically, FTIR spectra are composed of several absorption bands, each corresponding to specific functional groups related to cellular components such as lipids, proteins, carbohydrates and nucleic acids.

FTIR spectroscopy is used for analysis of various compounds in blood plasma such as total proteins, creatinine, amino acids, fatty acids, albumin, glucose, fibrinogen, lactate, triglycerides, glycerol, urea, triglycerides, cholesterol, apolipoprotein and immunoglobulin.

Additionally, FTIR spectroscopy is commonly used to distinguish between normal and abnormal tissue by analyzing the changes in absorption bands of macromolecules such as lipids, proteins, carbohydrates and nucleic acids. Additionally, FTIR spectroscopy may be utilized for evaluation of cell death mode, cell cycle progression, and the degree of maturation of hematopoietic cells.

SUMMARY OF EMBODIMENTS OF THE INVENTION

In some applications of the present invention, a method and system are provided for the diagnosis and monitoring of multiple types of malignant neoplasms, particularly malignant solid tumors.

Additionally or alternatively, some applications of the present invention comprise diagnosis and monitoring of a pre-malignant condition.

Typically, the method comprises analysis of blood plasma samples from cancer patients by techniques of infrared (IR) spectroscopy, for example, FTIR spectroscopy and/or microspectroscopy. As provided by applications of the present invention, FTIR Optical Diagnosis Technology (FODT) allows analysis of biochemical changes in a blood plasma sample of a patient which can indicate the presence of a solid tumor. Processes such as carcinogenesis may trigger changes in a biochemical composition of a body fluid of a patient, e.g., blood plasma. These changes are typically represented by differences in the absorption and reflection spectra when analyzed by FTIR spectroscopy techniques and compared to plasma samples from control individuals who do not suffer from a malignant solid tumor, e.g., healthy controls.

Accordingly, biochemical analysis of blood plasma samples obtained from untreated cancer patients and control individuals who do not suffer from a malignant solid tumor is conducted by FTIR microspectroscopy (FTIR MSP) techniques. Subsequently, the FTIR spectra (absorption and/or reflection) of blood plasma samples of the cancer patients are compared to the FTIR spectra of blood plasma samples obtained from the controls.

The inventors have identified that the blood plasma samples obtained from cancer patients suffering from a malignant solid tumor produce FTIR spectra that differ from those of the control individuals who do not suffer from a malignant solid tumor, allowing distinguishing between the cancer patients and controls. Thus, some applications of the present invention can be used to diagnose cancer patients suffering from various types of malignancies, particularly solid tumors. The distinction by FTIR spectroscopy between controls and patients suffering from solid tumors is typically performed based on analysis of blood plasma samples and not of the actual tumor cells.

For some applications, a data processor is configured to analyze the IR spectrum, e.g., the FTIR spectrum, of the blood plasma sample of a subject and an output unit is configured to generate an output indicative of the presence of a solid tumor, based on the infrared (IR) spectrum. Additionally, the data processor is typically configured to calculate a second derivative of the infrared (IR) spectrum of the blood plasma sample and, based on the second derivative of the infrared (IR) spectrum, to generate an output indicative of the presence of a solid tumor.

Additionally, some applications of the present invention allow distinguishing between various types of solid tumors. For example, blood plasma samples obtained from a cancer patient suffering from a certain type of solid tumor produces an FTIR spectrum having a unique spectral pattern which is characteristic of the type of malignancy and distinct from spectra of other malignancy types.

For some applications, analysis by IR spectroscopy, e.g., FTIR spectroscopy of the biochemistry of blood plasma samples can be used for the screening of large populations, aiding in the early detection of cancer, including solid tumors. Infrared (IR) spectroscopy and microspectroscopy techniques (e.g., FTIR spectroscopy or FTIR Microspectroscopy) as described herein are typically simple, reagent-free and rapid methods, suitable for use as screening tests for large populations. Early detection of cancer generally enables early intervention and treatment, contributing to a reduced mortality rate.

There is therefore provided in accordance with some applications of the present invention a method including:

obtaining an infrared (IR) spectrum of a blood plasma sample by analyzing the blood plasma sample by infrared spectroscopy; and based on the infrared spectrum, generating an output indicative of the presence of a solid tumor or a pre-malignant condition.

For some applications, generating the output includes generating the output indicative of the presence of the solid tumor.

For some applications, analyzing the blood plasma sample by infrared (IR) spectroscopy includes analyzing the blood plasma sample by Fourier Transformed Infrared (FTIR) spectroscopy, and obtaining the infrared (IR) spectrum includes obtaining a Fourier Transformed Infrared (FTIR) spectrum.

For some applications, analyzing the blood plasma sample by infrared (IR) spectroscopy includes analyzing the blood plasma sample by Fourier Transformed Infrared microspectroscopy (FTIR-MSP).

For some applications, analyzing includes assessing a characteristic of the blood plasma sample at least one wavenumber selected from the group consisting of: 759±4 cm−1, 987±4 cm−1, 1172±4 cm−1, 1270±4 cm−1, 1283±4 cm−1, and 1393±4 cm−1.

For some applications, analyzing includes assessing the characteristic at at least two wavenumbers selected from the group.

For some applications, analyzing includes assessing the characteristic at at least three wavenumbers selected from the group.

For some applications, analyzing includes assessing a characteristic of the blood plasma sample at at least one wavenumber selected from the group consisting of: 743±4 cm−1, 793±4 cm−1, 808±4 cm−1, 847±4 cm−1, 850±4 cm−1, 895±4 cm−1, 950±4 cm−1, 961±4 cm−1, 963±4, 967±4 cm−1, 975±4 cm−1, 997±4 cm−1, 1008±4 cm−1, 1030±4 cm−1, 1031±4 cm−1, 1048±4 cm−1, 1120±4 cm−1, 1150±4 cm−1, 1159±4 cm−1, 1188±4 cm−1, 1205±4 cm−1, 1220±4 cm−1, 1221±4 cm−1, 1255±4 cm−1, 1322±4 cm−1, 1326±4 cm−1, 1341±4 cm−1, 1356±4 cm−1 1370±4 cm−1, 1372±4 cm−1, 1402±4 cm−1, 1415±4 cm−1, and 1555±4 cm−1, 1595±4 cm−1, 1653±4 cm−1, 1681±4 cm−1.

For some applications, analyzing includes assessing the characteristic at at least two wavenumbers selected from the group.

For some applications, analyzing includes assessing the characteristic at at least three wavenumbers selected from the group.

For some applications, assessing the characteristic includes analyzing a band of the IR spectrum at at least one wavenumber selected from the group.

For some applications, the solid tumor includes a solid tumor in an organ selected from the group consisting of: lung, pancreas, prostate, bladder, and gastrointestinal tract, and generating the output includes generating an output indicative of the presence of a solid tumor in an organ selected from the group.

For some applications, the solid tumor includes breast cancer, and generating the output includes generating an output indicative of the presence of breast cancer.

For some applications, analyzing the blood plasma sample includes obtaining a second derivative of the infrared (IR) spectrum of the blood plasma sample.

For some applications, the blood plasma sample includes a dried blood plasma sample and analyzing the blood plasma sample includes analyzing the dried blood plasma sample.

For some applications, the infrared (IR) spectrum includes an absorption spectrum and obtaining the infrared (IR) spectrum includes obtaining the absorption spectrum.

For some applications, the infrared (IR) spectrum includes a reflection spectrum and obtaining the infrared (IR) spectrum includes obtaining the reflection spectrum.

There is further provided in accordance with some applications of the present invention a method for monitoring the effect of an anti-cancer treatment on a subject undergoing anti-cancer treatment for a solid tumor, for use with a first blood plasma sample separated from blood of the subject that was obtained prior to initiation of the treatment and a second blood plasma sample separated from blood of the subject that was obtained after initiation of the treatment, the method including:

obtaining IR spectra of the first and second blood plasma samples by analyzing the first and second blood plasma samples by IR spectroscopy; and based on the IR spectra, generating an output indicative of the effect of the treatment.

For some applications, analyzing the first and second blood plasma samples by IR spectroscopy includes analyzing the samples by Fourier Transformed Infrared spectroscopy, and obtaining the IR spectra includes obtaining Fourier Transformed Infrared (FTIR) spectra.

For some applications, analyzing the first and second blood plasma samples by infrared (IR) spectroscopy includes analyzing the first and second blood plasma samples by Fourier Transformed Infrared microspectroscopy (FTIR-MSP).

For some applications the method includes, obtaining an IR spectrum of a third blood plasma sample separated from blood of the subject that was obtained following termination of the treatment, by analyzing the third blood plasma sample by IR spectroscopy.

For some applications, analyzing includes assessing a characteristic of the blood plasma sample at at least one wavenumber selected from the group consisting of: 759±4 cm−1, 987±4 cm−1, 1172±4 cm−1, 1270±4 cm−1, 1283±4 cm−1, and 1393±4 cm−1.

For some applications, analyzing includes assessing the characteristic at at least two wavenumbers selected from the group.

For some applications, analyzing includes assessing the characteristic at at least three wavenumbers selected from the group.

For some applications, analyzing includes assessing a characteristic of the blood plasma sample at at least one wavenumber selected from the group consisting of: 743±4 cm−1, 793±4 cm−1, 808±4 cm−1, 847±4 cm−1, 850±4 cm−1, 895±4 cm−1, 950±4 cm−1, 961±4 cm−1, 963±4, 967±4 cm−1, 975±4 cm−1, 997±4 cm−1, 1008±4 cm−1, 1030±4 cm−1, 1031±4 cm−1, 1048±4 cm−1, 1120±4 cm−1, 1150±4 cm−1, 1159±4 cm−1, 1188±4 cm−1, 1205±4 cm−1, 1220±4 cm−1, 1221±4 cm−1, 1255±4 cm−1, 1322±4 cm−1, 1326±4 cm−1, 1341±4 cm−1, 1356±4 cm−1 1370±4 cm−1, 1372±4 cm−1, 1402±4 cm−1, 1415±4 cm−1, and 1555±4 cm−1, 1595±4 cm−1, 1653±4 cm−1, 1681±4 cm−1.

For some applications, analyzing includes assessing the characteristic at at least two wavenumbers selected from the group.

For some applications, analyzing includes assessing the characteristic at at least three wavenumbers selected from the group.

There is additionally provided in accordance with some applications of the present invention a method including:

obtaining an infrared (IR) spectrum of a blood plasma sample by analyzing the blood plasma sample; and based on the infrared spectrum, generating an output indicative of the presence of a solid tumor or a pre-malignant condition.

For some applications, generating the output includes generating the output indicative of the presence of the solid tumor.

There is yet additionally provided in accordance with some applications of the present invention, a system for diagnosing a solid tumor, including:

a data processor, configured to analyze an infrared (IR) spectrum of a blood plasma sample of a subject; and an output unit, configured to generate an output indicative of the presence of a solid tumor, based on the infrared (IR) spectrum.

For some applications, the data processor is configured to calculate a second derivative of the infrared (IR) spectrum of the blood plasma sample and, based on the second derivative of the infrared (IR) spectrum, to generate an output indicative of the presence of a solid tumor.

For some applications, the IR spectrum includes a Fourier Transformed Infrared (FTIR) spectrum, and the data processor is configured to calculate a second derivative of the FTIR spectrum.

For some applications, the data processor is configured to analyze the infrared (IR) spectrum by assessing a characteristic of the blood plasma sample at at least one wavenumber selected from the group consisting of: 759±4 cm−1, 987±4 cm−1, 1172±4 cm−1, 1270±4 cm−1, 1283±4 cm−1, and 1393±4 cm−1.

For some applications, the data processor is configured to analyze the infrared (IR) spectrum by assessing the characteristic at at least two wavenumbers selected from the group.

For some applications, the data processor is configured to analyze the infrared (IR) spectrum by assessing the characteristic at at least three wavenumbers selected from the group.

For some applications, the data processor is configured to analyze the infrared (IR) spectrum by assessing a characteristic of the blood plasma sample at at least one wavenumber selected from the group consisting of: 743±4 cm−1, 793±4 cm−1, 808±4 cm−1, 847±4 cm−1, 850±4 cm−1, 895±4 cm−1, 950±4 cm−1, 961±4 cm−1, 963±4, 967±4 cm−1, 975±4 cm−1, 997±4 cm−1, 1008±4 cm−1, 1030±4 cm−1, 1031±4 cm−1, 1048±4 cm−1, 1120±4 cm−1, 1150±4 cm−1, 1159±4 cm−1, 1188±4 cm−1, 1205±4 cm−1, 1220±4 cm−1, 1221±4 cm−1, 1255±4 cm−1, 1322±4 cm−1, 1326±4 cm−1, 1341±4 cm−1, 1356±4 cm−1 1370±4 cm−1, 1372±4 cm−1, 1402±4 cm−1, 1415±4 cm−1, and 1555±4 cm−1, 1595±4 cm−1, 1653±4 cm−1, 1681±4 cm−1.

For some applications, the data processor is configured to analyze the infrared (IR) spectrum by assessing the characteristic at at least two wavenumbers selected from the group.

For some applications, the data processor is configured to analyze the infrared (IR) spectrum by assessing the characteristic at at least three wavenumbers selected from the group.

There is still additionally provided in accordance with some applications of the present invention, a computer program product for administering processing of a body of data, the product including a computer-readable medium having program instructions embodied therein, which instructions, when read by a computer, cause the computer to:

obtain an infrared (IR) spectrum of a blood plasma sample by analyzing the blood plasma sample by infrared spectroscopy; and based on the infrared spectrum, generate an output indicative of the presence of a solid tumor.

The present invention will be more fully understood from the following detailed description of embodiments thereof, taken together with the drawings, in which:

DETAILED DESCRIPTION OF THE EMBODIMENTS

Figure 1A:
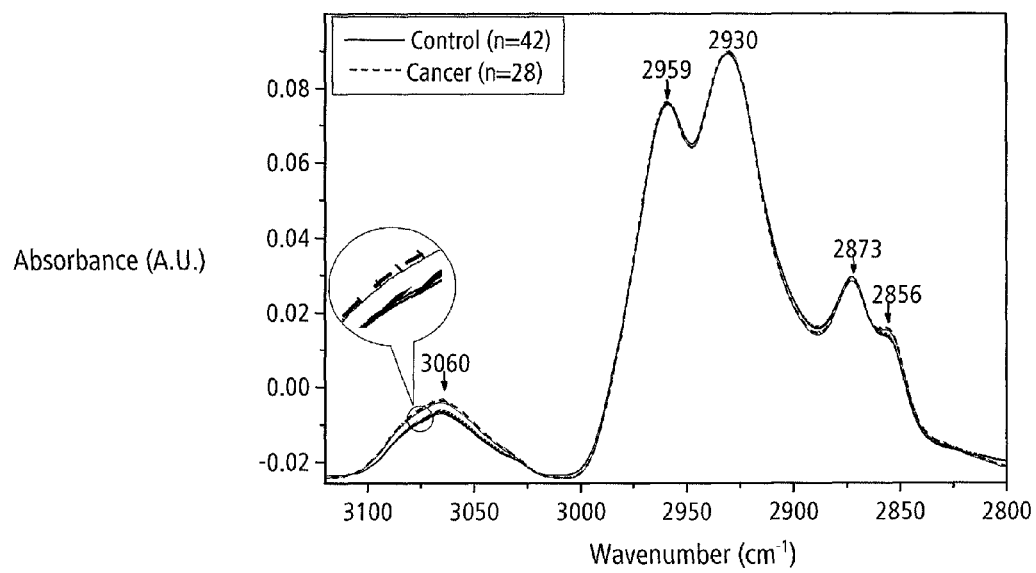
FIGS. 1A-F are graphs representing FTIR absorption spectra and the second derivative of absorption spectra and analysis thereof, based on blood plasma from several cancer patients and controls, derived in accordance with some applications of the present invention.

Some applications of the present invention comprise diagnosis of a solid tumor by FTIR microspectroscopy (MSP) techniques. For some applications, FTIR Optical Diagnosis Technology (FODT) is used to diagnose a solid tumor based on biochemical properties of a blood plasma sample of a subject. Some applications of the present invention comprise obtaining a blood sample from a subject and analyzing plasma from the sample by FTIR-MSP techniques for the detection of a malignancy, specifically a solid tumor. Typically, blood plasma of a patient suffering from a solid tumor is identified as exhibiting FTIR spectra that are different from FTIR spectra produced by blood plasma from a subject who does not suffer from a solid tumor (for some applications the control group may include subjects suffering from a pathology that is not a solid tumor). Accordingly, some applications of the present invention provide a useful method for the detection of cancer, specifically solid tumors. FTIR spectra of a blood plasma sample obtained from a cancer patient with a solid tumor generally reflect biochemical changes which occur in the blood plasma of the patient in response to the tumor.

For some applications, methods of the present invention are used to diagnose a type of solid tumor and/or a stage of the cancer.

For some applications, methods of the present invention can be used to provide monitoring and follow up of cancer patients during and after treatment, e.g., chemotherapy treatment. Typically, changes in FTIR spectra of blood plasma samples of solid-tumor patients who are undergoing treatment can indicate biochemical changes in response to the treatment. This biochemical information can provide insight into the effect of treatment on the patient and/or the tumor. Methods Used in Some Embodiments of the Present Invention A series of protocols are described hereinbelow which may be used separately or in combination, as appropriate, in accordance with applications of the present invention. It is to be appreciated that numerical values are provided by way of illustration and not limitation. Typically, but not necessarily, each value shown is an example selected from a range of values that is within 20% of the value shown. Similarly, although certain steps are described with a high level of specificity, a person of ordinary skill in the art will appreciate that other steps may be performed, mutatis mutandis.

In accordance with some applications of the present invention, the following methods were applied:
Obtaining Patient and Control Populations All studies were approved by the local Ethics Committee of the Soroka University Medical Center and conducted in accordance with the Declaration of Helsinki. Qualified personnel obtained informed consent from each individual participating in this study.

The patient population included 28 cancer patients diagnosed with the following primary tumors:

Breast (n=13), lung (n=4), pancreas (n=1), prostate (n=1) bladder (n=1), and gastrointestinal (n=7) and unknown origin (n=1) cancers.

The diagnosis of cancer was determined by clinical, surgical, histological, and pathologic diagnosis. The pathologic stage of the tumor was determined according to tumor-node-metastasis (TNM) classification, as described in "TNM Classification of Malignant Tumours", by Sobin LH. et al., 7th Edition, New York: John Wiley, 2009. A control group (n=42) included healthy volunteers who underwent detailed clinical questioning, at the Soroka University Medical Center and Ben-Gurion University.

Collection of Blood Samples 1-2 ml of peripheral blood was collected in 5 ml EDTA blood collection tubes (BD Vacutainer® Tubes, BD Vacutainer, Toronto) from patients and healthy controls using standard phlebotomy procedures. Samples were processed within 2 hours of collection. It is to be noted that any other suitable anticoagulant may be used in collection and processing of the blood samples.

Isolation of Plasma from Peripheral Blood Samples

Blood from cancer patients and healthy controls was diluted 1:1 in isotonic saline (0.9% NaCl solution). The diluted blood was applied carefully to Histopaque 1077 gradients (Sigma Chemical Co., St. Louis, Mo., USA) in 15 ml collection tubes, and centrifuged at 400 g for 30 min.

To discard platelets and cell debris, the plasma was transferred to 1.5 ml eppendorf tubes and centrifuged at 3,200 g for 10 min. The supernatant was transferred to a new eppendorf tube, and 0.5 µl of plasma was deposited on a zinc selenide (ZnSe) slide. It is noted that any other suitable slide may be used, e.g., reflection measurements may be carried out using a gold slide. The slide was air dried for 1 hour under laminar flow to remove water. The dried plasma was then subjected to FTIR microscopy.

FTIR-Microspectroscopy

Fourier Transform Infrared Microspectroscopy (FTIR-MSP) and Data Acquisition Measurements were performed using the FTIR microscope Nicolet Centaurus with a liquid-nitrogen-cooled mercury-cadmium-telluride (MCT) detector, coupled to the FTIR spectrometer Nicolet iS10, OMNIC software (Nicolet, Madison, Wis.) using OPUS software (Bruker Optik GmbH, Ettlingen, Germany). To achieve high signal-to-noise ratio (SNR), 128 coadded scans were collected in each measurement in the wavenumber region 700 to 4000 cm−1. The measurement site was circular, with a diameter of 100 µm and spectral resolution of 4 cm−1 (0.482 cm−1 data spacing). To reduce plasma sample thickness variation and achieve proper comparison between different samples, the following procedures were adopted:

1. Each sample was measured at least five times at different spots.
2. Analog to Digital Converter (ADC) rates were empirically chosen between 2000 to 3000 counts/sec (providing measurement areas with similar material density).
3. The obtained spectra were baseline corrected using the rubber band method, with 64 consecutive points, and normalized using vector normalization in OPUS software as described in an article entitled "Early spectral changes of cellular malignant transformation using Fourier transformation infrared microspectroscopy", by Bogomolny et al., 2007. J. Biomed Opt. 12:024003.

In order to obtain precise absorption values at a given wavenumber with minimal background interference, the second derivative spectra were used to determine concentrations of bio-molecules of interest. This method is susceptible to changes in FWHM (full width at half maximum) of the IR bands. However, in the case of biological samples, all samples (plasma) from the same type are composed of similar basic components, which give relatively broad bands. Thus, it is possible to generally neglect the changes in band FWHM, as described in an article entitled "Selenium alters the lipid content and protein profile of rat heart: An FTIR microspectroscopy study", by Toyran et al., Arch. Biochem. Biophys. 2007 458:184-193.

Statistical Analysis:

Statistical analysis was performed using the student T-test. P-values<0.05 were considered significant. Statistical analysis was performed using STATISTICA software (STATISTICA, StatSoft, Inc., Tulsa, Okla.).

Artificial Neural Network Analysis:

Alyuda NeuroIntelligence 2.2 (Alyuda Research Inc.) is a Neural Network Software for Classifying Data.

EXPERIMENTAL DATA

The experiments described hereinbelow were performed by the inventors in accordance with applications of the present invention, and using the techniques described hereinabove.

In a set of experiments, blood plasma from 42 healthy controls was analyzed by FTIR-MSP, and a typical FTIR-MSP spectral pattern was established for control blood plasma. Additionally, blood plasma samples from 28 cancer patients suffering from multiple types of solid tumors were subjected to FTIR-MSP analysis and compared to the control FTIR-MSP spectral pattern. The blood plasma was obtained by preliminary processing of the peripheral blood in accordance with the protocols described hereinabove with reference to isolation of plasma from peripheral blood samples. The blood plasma samples were then analyzed by FTIR-MSP in accordance with the protocols described hereinabove with reference to FTIR-MSP.

Reference is made to FIGS. 1A-F, which are graphs representing FTIR absorption spectra and the second derivative of absorption spectra and analysis thereof, for blood plasma from 28 cancer patients and 42 healthy controls, derived in accordance with some applications of the present invention.

Figure 1B:
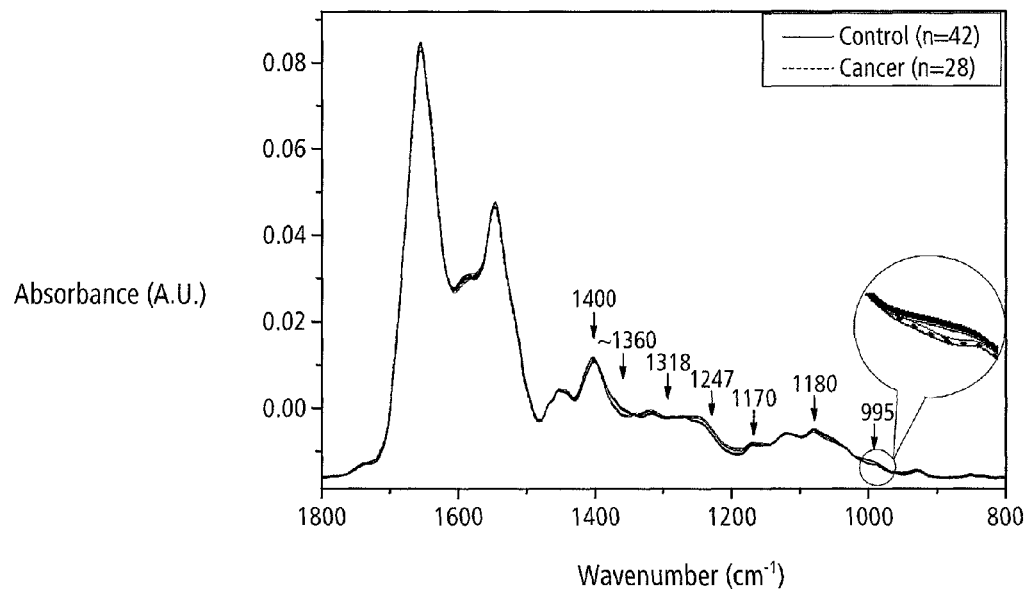

FTIR-MSP analysis of blood plasma typically generated spectra in the region of 4000-700 cm−1. The spectra are composed of several absorption bands, each corresponding to specific functional groups of specific macromolecules. FIGS. 1A-B show average FTIR-MSP spectra of blood plasma of healthy controls and cancer patients in the regions of 3150-2830 cm−1 (FIG. 1A) and 1800-700 cm−1 (FIG. 1B), after baseline correction and vector normalization. The main absorption bands are marked and the mean±SEM is represented by the gray region around the average solid (control) and dotted (cancer) lines The absorption bands observed in the FTIR spectra shown in FIGS. 1A-B generally correspond to vibrations of functional groups of molecules which are present in blood plasma. For example, proteins (e.g., albumin and globulins), nutrients (e.g., glucose, amino acids, fatty acids, and monoglycerides) fibrinogen, electrolytes, solutes, hormones, enzymes, vitamins and other cellular components; each has its own spectral fingerprint that together compose the entire spectra of the plasma sample. Each spectrum of a single plasma sample represents the average of five measurements at different sites for each sample.

As shown in FIGS. 1A-B, the FTIR-MSP spectra derived from analysis of blood plasma from the cancer patients exhibited a different spectral pattern when compared to the FTIR-MSP spectra of blood plasma of healthy controls.

Reference is made to FIG. 1A. Typically, the spectral region 3150-2830 cm−1 contains absorption bands due to symmetric and asymmetric CH3 (at 2959 cm−1, 2873 cm−1) and CH3 (at 2930 cm−1, 2856 cm−1) stretching vibrations corresponding mainly to proteins and lipids respectively. Another absorption band located at ~3060 cm−1 in this region typically is due to N—H stretching, and corresponds to Amide B. The absorption at the band corresponding to Amide B was found to be significantly higher (p<2*10^−4) in the blood plasma samples of cancer patients when compared to blood plasma from the healthy controls, as revealed by calculation of the area under the Amide B band (at 3014 cm−1 to 3110 cm−1) following cut, baseline correction and Min-Max normalization at 2800 cm−1 to 3150 cm−1.

Reference is made to FIG. 1B which shows a spectral region of 1800-700 cm−1. Additionally, the insert in FIG. 1B shows a detailed view of the 1400-900 cm−1 spectral region which has several overlapping bands which correspond to multiple functional groups of plasma components. The detailed view of the 1400-900 cm−1 spectral region shows several differences between blood plasma samples of cancer patients compared to healthy controls, e.g., a reduction at 1400 cm−1 (containing COO− symmetric stretch) typically corresponding to protein.

Figure 1C:
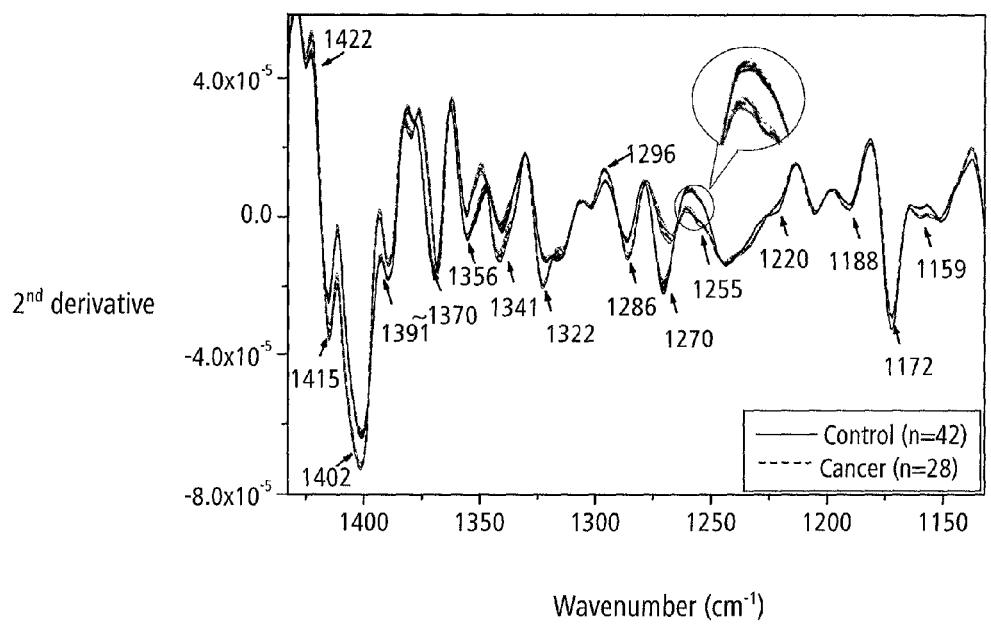
Figure 1D:
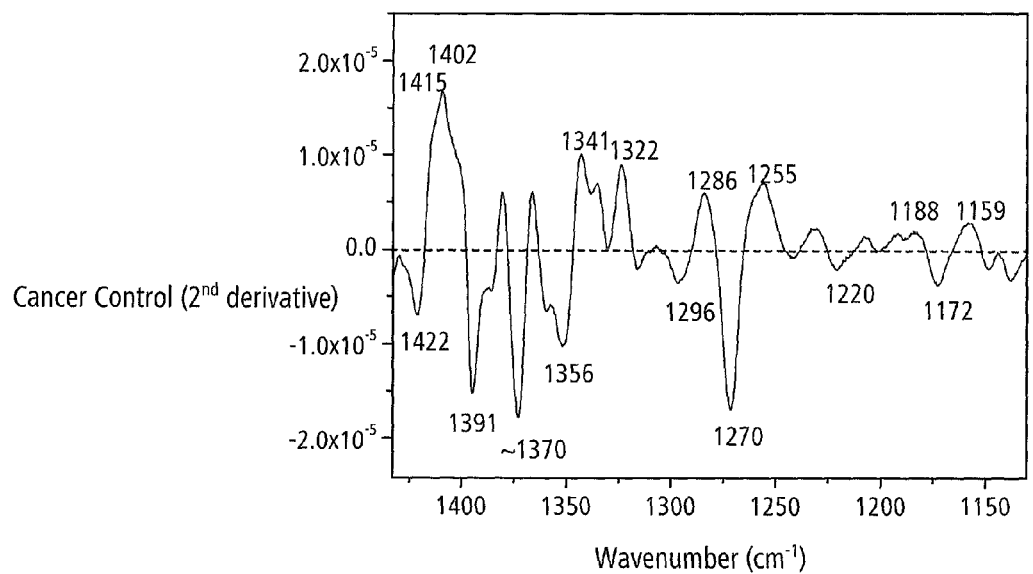
Figure 1E:
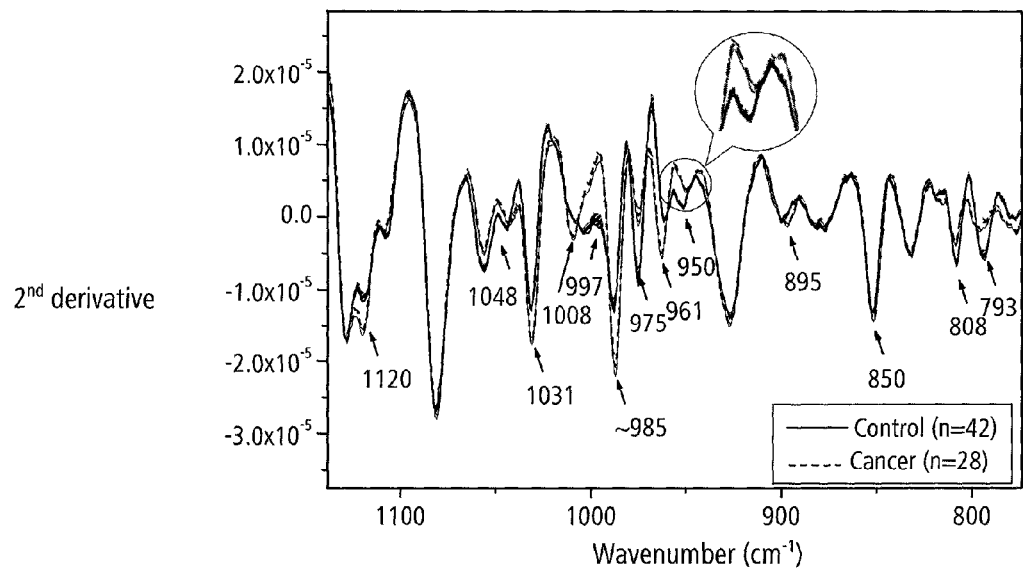

Reference is made to FIGS. 1C and 1E. In order to increase accuracy and achieve effective comparison between the blood plasma samples of the cancer patients and the healthy controls, the second derivative of the baseline-corrected, vector-normalized FTIR spectra was used. Results are presented in FIGS. 1C and 1E. As shown, the second derivative spectral pattern of blood plasma samples from the cancer patients differed significantly from the FTIR-MSP spectral pattern of blood plasma of the healthy controls. The main absorption bands are marked and the mean±SEM is represented by the gray area around the solid (controls) and dotted (cancer) lines.

Figure 1F:
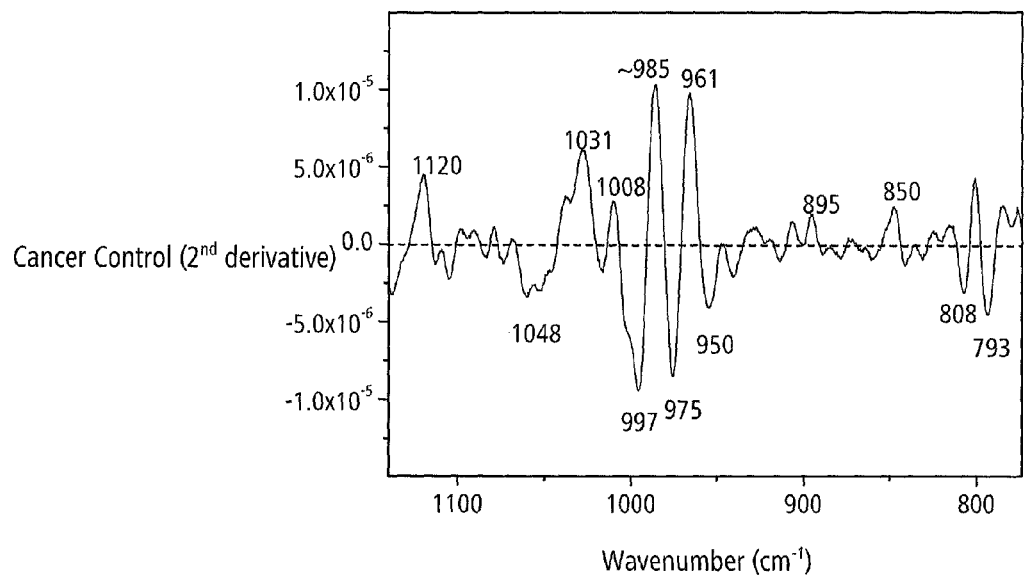

Reference is made to FIGS. 1D and 1F, which are graphs showing an analysis of the second derivative data shown in FIGS. 1C and 1E. The graphs in FIGS. 1D and 1F represent the variation between the second derivative of the spectral pattern of blood plasma samples from the cancer patients and healthy controls, obtained in accordance with applications of the present invention.

Figure 2:
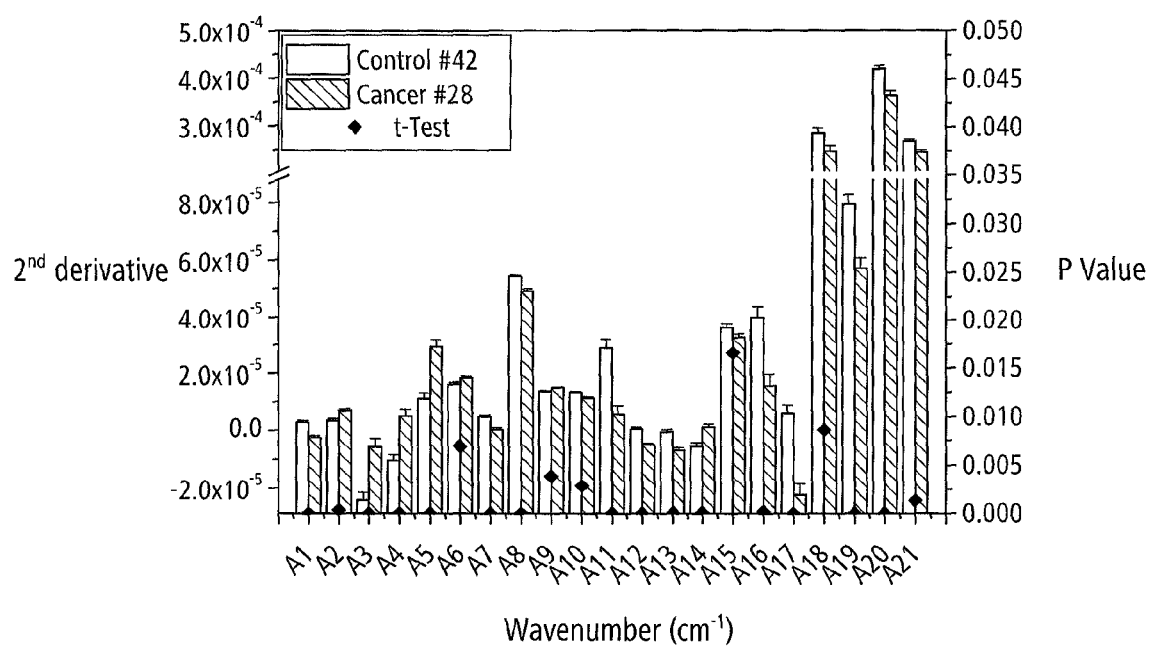
FIG. 2 is a graph representing values of the second derivative of absorption spectra of blood plasma samples from cancer patients compared to blood plasma samples from healthy controls, derived in accordance with some applications of the present invention.

FIG. 2 shows a graph representing values of the second derivative of absorption spectra at wavenumbers A1-A21 of blood plasma samples from cancer patients compared to blood plasma samples from healthy controls, derived in accordance with some applications of the present invention. Statistical analysis was performed and P-values are provided. As shown, the second derivative of blood plasma from the cancer patients differed significantly from the second derivative analysis of FTIR-MSP spectral pattern from blood plasma of healthy controls.

Table I lists the wavenumbers shown in FIG. 2. Typically, blood plasma samples were analyzed by FTIR-MSP techniques using these wavenumbers to distinguish between healthy controls and cancer patients.

TABLE I

| | Wavenumber (cm−1) ± 4 |
|---|---|
| A1 | 743 |
| A2 | 759 |
| A3 | 847 |
| A4 | 963 |
| A5 | 967 |
| A6 | 987 |
| A7 | 1030 |
| A8 | 1150 |
| A9 | 1172 |
| A10 | 1205 |
| A11 | 1221 |
| A12 | 1270 |
| A13 | 1283 |
| A14 | 1326 |
| A15 | 1356 |
| A16 | 1372 |
| A17 | 1393 |
| A18 | 1555 |
| A19 | 1595 |
| A20 | 1653 |
| A21 | 1681 |

The data obtain by analysis of the blood plasma samples may be further analyzed by any suitable method known in the art, e.g., Artificial Neural Network and/or Cluster Analysis, and/or Principal Component Analysis, and/or Linear Discriminant Analysis (LDA) and/or Non Linear Discriminant Analysis.

For example, data obtained in accordance with applications of the present invention was analyzed by artificial neural network (ANN). Several biomarkers shown in Table I which were statistically significant (p<0.05) were served as an input vector for the ANN analysis. According to the ANN, 2 spectra out of 42 controls were rejected from the analysis. These two spectra were suspected for improper sample preparation. Twenty eight spectra were randomly selected for training, 17 for validation and 23 for test. This procedure was repeated at least ten times (each time with different sets for training, test and validation) to confirm repeatability of the results. All of the ANN analysis results presented high sensitivity and specificity of about 85% and 90%, respectively.

Reference is made to FIGS. 1 and 2.

It is further noted that the scope of the present invention includes the use of only one wavenumber biomarker for detection and/or monitoring of a solid tumor, as well as the use of two, three, four, or more wavenumbers.

Additionally, the scope of the present invention includes using any IR spectral feature or any feature derived from analysis of an IR spectral feature (e.g., any type of peak analysis), to indicate the presence of a solid tumor.

It is also noted that the scope of the present invention is not limited to any particular form or analysis of IR spectroscopy. For example, IR spectroscopy may include Attenuated Total Reflectance (ATR) spectroscopy techniques.

Although applications of the present invention are described hereinabove with respect to spectroscopy, microspectroscopy, and particularly FTIR spectroscopy, the scope of the present invention includes the use of analysis techniques with data obtained by other means as well (for example, using a monochromator or an LED, at specific single wavenumbers, and/or FTIR imaging).

It is additionally noted that the scope of the present invention is not limited to blood plasma and may apply to any treated or untreated blood component. For example, techniques and methods described herein may alternatively be applied to blood serum.

It will be understood by one skilled in the art that aspects of the present invention described hereinabove can be embodied in a computer running software, and that the software can be supplied and stored in tangible media, e.g., hard disks, floppy disks, a USB flash drive, or compact disks, or in intangible media, e.g., in an electronic memory, or on a network such as the Internet.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for indicating whether a subject has a gastrointestinal tract solid tumor, the method comprising:
    isolating, using a gradient, a blood plasma sample from a peripheral blood sample taken from the subject;
    drying, using a dryer, the blood plasma sample of the subject;
    measuring an infrared (IR) spectrum of the dried blood plasma sample of the subject by analyzing the dried blood plasma sample by infrared spectroscopy, and assessing a characteristic of the dried blood plasma sample at at least one wavenumber selected from the group consisting of: 847±4 cm−1, 1150±4 cm−1, 1205±4 cm−1, 1356±4 cm−1, and 1372±4 cm−1;
    using a data processor, comparing at the at least one wavenumber (a) the infrared spectrum of the dried blood plasma sample of the subject to (b) an infrared spectrum obtained from a dried plasma sample from a person without a solid tumor, to detect a difference between the infrared spectrum of the dried plasma sample of the subject and the infrared spectrum obtained from the dried plasma sample from the person without a solid tumor; and
    based on the comparing, generating an output indicative of the presence of a gastrointestinal tract solid tumor in the subject.

2. The method according to claim 1, wherein analyzing the dried blood plasma sample by infrared (IR) spectroscopy comprises analyzing the dried blood plasma sample by Fourier Transformed Infrared (FTIR) spectroscopy, and wherein measuring the infrared (IR) spectrum comprises measuring a Fourier Transformed Infrared (FTIR) spectrum.

3. The method according to claim 2, wherein analyzing the dried blood plasma sample by infrared (IR) spectroscopy comprises analyzing the dried blood plasma sample by Fourier Transformed Infrared microspectroscopy (FTIR-MSP).

4. The method according to claim 1, wherein assessing the characteristic further comprises assessing a characteristic of the dried blood plasma sample at at least one wavenumber selected from the group consisting of: 759±4 cm−1, 987±4 cm−1, 1172±4 cm−1, 1270±4 cm−1, 1283±4 cm−1, and 1393±4 cm−1.

5. The method according to claim 1, wherein analyzing comprises assessing the characteristic at at least two wavenumbers selected from the group.

6. The method according to claim 1, wherein assessing the characteristic further comprises assessing a characteristic of the dried blood plasma sample at at least one wavenumber selected from the group consisting of: 743±4 cm−1, 793±4 cm−1, 808±4 cm−1, 850±4 cm−1, 895±4 cm−1, 950±4 cm−1, 961±4 cm−1, 963±4, 967±4 cm−1, 975±4 cm−1, 997±4 cm−1, 1008±4 cm−1, 1030±4 cm−1, 1031±4 cm−1, 1048±4 cm−1, 1120±4 cm−1, 1159±4 cm−1, 1188±4 cm−1, 1220±4 cm−1, 1221±4 cm−1, 1255±4 cm−1, 1322±4 cm−1, 1326±4 cm−1, 1341±4 cm−1, 1370±4 cm−1, 1402±4 cm−1, 1415±4 cm−1, and 1555±4 cm−1, 1595±4 cm−1, 1653±4 cm−1, 1681±4 cm−1.

7. The method according to claim 1, wherein assessing the characteristic comprises analyzing a band of the IR spectrum at the at least one wavenumber selected from the group.

8. The method according to claim 1, wherein analyzing the dried blood plasma sample comprises obtaining a second derivative of the infrared (IR) spectrum of the dried blood plasma sample.

9. A system for indicating whether a subject has a gastrointestinal tract solid tumor, the system comprising:
    a gradient configured to isolate a blood plasma sample from a peripheral blood sample of the subject;
    a dryer configured to dry the blood plasma sample;
    a data processor, configured (i) to analyze an infrared (IR) spectrum of the dried blood plasma sample of the subject by assessing a characteristic of the dried blood plasma sample at at least one wavenumber selected from the group consisting of: 847±4 cm−1, 1150±4 cm−1, 1205±4 cm−1, 1356±4 cm−1, and 1372±4 cm−1, and (ii) to compare at the at least one wavenumber (a) the infrared spectrum of the dried blood plasma sample of the subject to (b) an infrared spectrum obtained from a dried plasma sample from a person without a solid tumor, to detect a difference between the infrared spectrum of the dried plasma sample of the subject and the infrared spectrum obtained from the dried plasma sample from the person without a solid tumor; and
    an output unit, configured to generate an output indicative of the presence of a gastrointestinal tract solid tumor in the subject, based on the comparing.

10. The system according to claim 9, wherein the data processor is configured to calculate a second derivative of the infrared (IR) spectrum of the dried blood plasma sample and, based on the second derivative of the infrared (IR) spectrum, to generate an output indicative of the presence of the gastrointestinal tract solid tumor.

11. The system according to claim 10, wherein the IR spectrum includes a Fourier Transformed Infrared (FTIR) spectrum, and wherein the data processor is configured to calculate a second derivative of the FTIR spectrum.

12. The system according to claim 9, wherein the data processor is further configured to analyze the infrared (IR) spectrum by assessing a characteristic of the dried blood plasma sample at at least one wavenumber selected from the group consisting of: 759±4 cm−1, 987±4 cm−1, 1172±4 cm−1, 1270±4 cm−1, 1283±4 cm−1, and 1393±4 cm−1.

13. The system according to claim 9, wherein the data processor is configured to analyze the infrared (IR) spectrum by assessing the characteristic at at least two wavenumbers selected from the group.

14. The system according to claim 9, wherein the data processor is further configured to analyze the infrared (IR) spectrum by assessing a characteristic of the dried blood plasma sample at at least one wavenumber selected from the group consisting of: 743±4 cm−1, 793±4 cm−1, 808±4 cm−1, 850±4 cm−1, 895±4 cm−1, 950±4 cm−1, 961±4 cm−1, 963±4, 967±4 cm−1, 975±4 cm−1, 997±4 cm−1, 1008±4 cm−1, 1030±4 cm−1, 1031±4 cm−1, 1048±4 cm−1, 1120±4 cm−1, 1159±4 cm−1, 1188±4 cm−1, 1220±4 cm−1, 1221±4 cm−1, 1255±4 cm−1, 1322±4 cm−1, 1326±4 cm−1, 1341±4 cm−1, 1370±4 cm−1,1402±4 cm−1, 1415±4 cm−1, and 1555±4 cm−1, 1595±4 cm−1, 1653±4 cm−1, 1681±4 cm−1.

15. A computer program product for administering processing of a body of data, the product comprising a computer-readable medium having program instructions embodied therein, which instructions, when read by a computer, cause the computer to:

measure an infrared (IR) spectrum of a dried blood plasma sample isolated from a peripheral blood sample of a subject, by analyzing the dried blood plasma sample by infrared spectroscopy;

assess a characteristic of the dried blood plasma sample at at least one wavenumber selected from the group consisting of: 847±4 cm−1, 1150±4 cm−1, 1205±4 cm−1, 1356±4 cm−1, and 1372±4 cm−1;

compare at the at least one wavenumber (a) the infrared spectrum of the dried blood plasma sample of the subject to (b) an infrared spectrum obtained from a dried plasma sample from a person without a solid tumor, to detect a difference between the infrared spectrum of the dried plasma sample of the subject and the infrared spectrum obtained from the dried plasma sample from the person without a solid tumor; and based on the comparison, generate an output indicative of the presence of a gastrointestinal tract solid tumor in the subject.

* * * * *